US011774391B2

(12) United States Patent
Spencer

(10) Patent No.: US 11,774,391 B2
(45) Date of Patent: Oct. 3, 2023

(54) GREASE INTERCEPTOR LEVEL ANALYZER

(71) Applicant: Water Analytics, Inc., Andover, MA (US)

(72) Inventor: Mark Spencer, Newburyport, MA (US)

(73) Assignee: Water Analytics, Inc., Andover, MA (US)

(*) Notice: Subject to any disclaimer, the term of this patent is extended or adjusted under 35 U.S.C. 154(b) by 0 days.

(21) Appl. No.: 17/726,214

(22) Filed: Apr. 21, 2022

(65) Prior Publication Data
US 2022/0244208 A1 Aug. 4, 2022

Related U.S. Application Data

(63) Continuation-in-part of application No. 16/728,196, filed on Dec. 27, 2019, now Pat. No. 11,340,096.

(60) Provisional application No. 62/786,801, filed on Dec. 31, 2018.

(51) Int. Cl.
G01N 27/22 (2006.01)

(52) U.S. Cl.
CPC ................. G01N 27/226 (2013.01)

(58) Field of Classification Search
None
See application file for complete search history.

(56) References Cited

U.S. PATENT DOCUMENTS

| 3,710,244 A | 1/1973 | Rauchwerger |
| 3,864,974 A | 2/1975 | Rauchwerger |
| 4,226,118 A | 10/1980 | Aldrich |
| 5,052,223 A | 10/1991 | Regnault et al. |
| 5,097,703 A | 3/1992 | Peter |
| 5,546,005 A | 8/1996 | Rauchwerger |
| 5,940,899 A * | 8/1999 | Mankin .................. E03D 11/00 73/304 C |
| 5,969,620 A | 10/1999 | Okulov |

(Continued)

FOREIGN PATENT DOCUMENTS

| CN | 107850475 A | 3/2018 |
| DE | 102013207446 A1 | 10/2014 |

(Continued)

OTHER PUBLICATIONS

Office Action for U.S. Appl. No. 16/728,196 dated Sep. 29, 2021, 17 Pages.

(Continued)

Primary Examiner — Paul M. West
Assistant Examiner — Mark A Shabman
(74) Attorney, Agent, or Firm — Walter F. Dawson; Maine Cernota & Rardin

(57) ABSTRACT

An analyzer for a grease interceptor for measuring identity of materials and levels of fat, oil, and grease (FOG), water, sludge and air having a probe which includes a controller and a sensor sub-unit. Sensor circuits include a microcontroller, timers, and sampling capacitors. The sensor sub-unit includes a plurality of electrode ring pairs coupled to a plurality of timers for converting capacitance measurements to frequencies under the control of a microprocessor in the controller. The frequencies identify the measured levels. A calibration of the probe converts a range of frequency values of each sensor circuit to an arbitrary scale for improved accuracy.

30 Claims, 8 Drawing Sheets

(56) References Cited

U.S. PATENT DOCUMENTS

| | | | |
|---|---|---|---|
| 6,125,696 A | 10/2000 | Hannan et al. | |
| 6,138,508 A * | 10/2000 | Hannan | G01F 23/266 73/304 C |
| 6,433,560 B1 * | 8/2002 | Hansen | G01F 23/266 324/668 |
| 6,619,118 B1 * | 9/2003 | Keck | G01F 23/242 73/304 C |
| 6,776,900 B2 * | 8/2004 | Mazurek | B01D 17/005 73/304 C |
| 6,879,935 B2 | 4/2005 | Keck | |
| 7,001,785 B1 | 2/2006 | Chen | |
| 7,933,733 B2 | 4/2011 | Ashrafzadeh et al. | |
| 8,215,166 B2 | 7/2012 | Cunningham et al. | |
| 8,943,911 B1 * | 2/2015 | Terrell | G01F 23/0007 73/865.8 |
| 9,638,653 B2 | 5/2017 | Potyrailo et al. | |
| 9,657,178 B2 * | 5/2017 | Cho | C08J 7/043 |
| 2008/0184795 A1 | 8/2008 | Woodward | |
| 2008/0229819 A1 | 9/2008 | Mayleben et al. | |
| 2009/0139325 A1 * | 6/2009 | Cunningham | G01D 5/24 73/304 C |
| 2010/0101317 A1 | 4/2010 | Ashrafzadeh et al. | |
| 2011/0036164 A1 | 2/2011 | Burdi | |
| 2011/0303004 A1 * | 12/2011 | Carson-Rowland | G01F 25/24 73/304 R |
| 2015/0198578 A1 | 7/2015 | Worden et al. | |

FOREIGN PATENT DOCUMENTS

| | | |
|---|---|---|
| DE | 102013010708 A1 | 12/2014 |
| EP | 2657663 A1 | 10/2013 |
| EP | 2663843 A1 | 11/2013 |
| FR | 2960549 B1 | 12/2011 |
| KR | 101060220 B1 | 8/2011 |
| KR | 101129924 B1 | 3/2012 |

OTHER PUBLICATIONS

Notice of Allowability for U.S. Appl. No. 16/728,196 dated Jan. 25, 2022, 8 pages.

Notice of Allowability for U.S. Appl. No. 16/728,196 dated Feb. 16, 2022, 6 pages.

* cited by examiner

GREASE INTERCEPTOR LEVEL ANALYZER

RELATED APPLICATIONS

This application is a Continuation-In-Part of U.S. application Ser. No. 16/728,196, filed Dec. 27, 2019, which claims the benefit of U.S. Provisional Applications No. 62/786,801, filed Dec. 31, 2018. Each of these applications is herein incorporated by reference, in its entirety, for all purposes.

BACKGROUND OF THE INVENTION

Field of the Invention

The invention relates generally to a grease interceptor or grease trap used where food is handled and served and in particular to a grease interceptor level analyzer for measuring the levels of fats, oils, grease, and sludge within the interceptor.

Description of Related Art

Grease interceptors, are required in all food service establishments (FSE). These include commercial kitchens, food service, food preparation and other facilities where food is handled and served to prevent fats, oil, and grease and solids/sludge from entering the sanitary sewer or septic system where it leads to blockages and contamination. Fats, oil, and grease are referred to as FOG and with solids as FOGS.

Grease interceptors refer to both small units that are located in or near the kitchen or larger units that are located buried in the ground exterior to the facility (i.e. in the parking lot). The term "grease trap" is often used as a colloquialism for "grease interceptor." The two terms are used interchangeably herein.

Referring to FIG. 1, a graphic illustration of a typical passive grease interceptor 10 in the prior art is show. Conventional grease interceptors are passive and rely on the specific gravity of the components of the wastewater 12 to separate. The wastewater 12 enters the trap and is typically piped to below the midpoint where it empties into the trap. The FOG 14 is lighter than water and floats to the top. Solids 18 settle to the bottom as sediment (or "sludge"). This creates a static level of liquids made up of 3 layers: sediment 18, water 12 and FOG 14. The water 12 portion exits the grease trap so that the total level of all three layers remains constant and the FOGS layers 14, 18 grows. The interceptor 10 must be emptied before the FOG 14 layer reaches the outlet 19 for the water. Municipalities regulate the maintenance of grease interceptors. One common regulation requires emptying the trap when the volumes of the FOG 14 plus solids layers reach 25% of the total volume.

The traditional core sampler, aka "Sludge Judge", requires opening up an interceptor, sticking in the sampler, waiting for the contents to settle and taking measurement with a ruler. It's dirty, smelly, prone to error and time-consuming. It cannot be automated and cannot be adapted to make real-time measurements. Though the upfront cost is low (approximately $200) the time required to conduct the measurement and clean and travel from site to site make the operating costs very high. Furthermore, the manual operation of this device prevents it from being automated.

The leading technology for electronic measurement of FOG levels is based on measuring layer interfaces using an ultrasonic transducer and receiver. This device fouls easily and is frequently "confused" by spurious reflections, such as walls and foam. The last drawback limits the use of ultrasonic analyzers to large interceptors. The majority of grease traps in restaurant kitchens are therefore unable to avail themselves of this technology. The underlying ultrasonic technology makes this device necessarily expensive and complex.

At least one commercialized FOG analyzer used the principle of resistivity to measure differences between FOG, water and sediment. This method is intrinsically simple and inexpensive. However, this type of device works only when the surfaces of the measuring electrodes are clean. In practice the oily environment of a grease trap quickly coats the electrodes and decreases the measured resistivity.

The capacitance-based FOG analyzer has distinct advantages over the above prior art such as: providing real-time level measurements, requiring only periodic opening of the grease traps when they are being serviced, providing a read-out that is easy to understand, allowing results to be sent automatically to a networked server, enabling much lower manufacturing costs than competing ultrasound-based analyzers. Furthermore, it is less susceptible to fouling than ultrasound-based analyzers, and it can be easily assembled to fit into any grease interceptor from small kitchen units to large outside ones.

In the prior art, U.S. Pat. No. 8,943,911 issued Feb. 3, 2015 to Mark C. Terrell discloses a system for remotely monitoring stratified layers in grease interceptors including a sensing unit for being disposed in a grease interceptor having a pair of elongated sensing rods and a plurality of spaced apart sensors in groups along the rod for sensing stratified layers in the grease interceptor, a wireless transmitter electrically coupled to the sensing unit and a central server for receiving acquired data transmitted by the wireless transmitter. However, the critical element in an accurate and successfully operating probe or monitor of stratified layers of the grease interceptor is the sensor. Terrell et al. does not teach or disclose an operational sensor such as the novel sensor of the present invention, and in fact opines that substantially any type of sensor that right now exists or hereafter be discovered may be used. Terrell does suggest use of sensors disclosed in U.S. Pat. Nos. 6,619,118 and 6,879,935.

U.S. Pat. No. 6,619,118 Issued Sep. 16, 2003 to James C. Kech discloses a septic tank monitoring system for distinguishing between and identifying the location of a sedimentary layer, a scum layer and any intervening liquid zone in a septic tank with an elongated sensing probe for being disposed in the septic tank. It discloses sensors that are relatively small, hemispherical electrode, or it could preferably be a ring electrode. However, it does not disclose the principle of operation of said sensors beyond calling them "electrodes" and suggesting that the sensors might, alternatively, measure temperature or pressure.

U.S. Pat. No. 6,879,935 issued Apr. 12, 2005, also to James C. Kech discloses a monitoring system for a septic tank to distinguish between and identifying a sedimentary layer, a scum layer, and any intervening liquid zone in a septic tank with an elongate sensing probe for measuring the differences in the layer's high frequency electrical conductivity using a plurality of sensors. As with U.S. Pat. No. 6,619,118 the principle of operation of sensors is not specified though a further elaboration is based on electrodes that measure conductivity and a second elaboration is based on thermistors that measure temperature. It shows a common electrode reference sensor is disposed on the elongated tube of the probe and could be a hemispherical electrode or a ring electrode. The other sensors spaced along the elongated tube are hemispherical, chemically inert sensor electrodes. However, the more accurate capacitance-based sensor structure of the present invention is not disclosed.

U.S. Pat. No. 8,215,166 issued Jul. 10, 2012 To J. Vern Cunningham et al. disclosed a capacitance-based FOG analyzer having a grease sensor and remote monitor unit. The device consisted of one pair of capacitance sensing electrodes incorporated into the printed circuit board that resides in the interior of the cylindrical housing. Such a design insufficient to reliably detect the positions of the FOG-water and water-sludge interfaces. Furthermore, its positioning in the center of the probe renders it less sensitive to changes in capacitance of the surrounding medium.

SUMMARY OF THE INVENTION

Accordingly it is therefore an object of this invention to provide a grease interceptor level analyzer for measuring levels of fats, oils, grease (FOG), water, sludge and air, this analyzer being embodied as a fixed probe and a portable probe It is another object of this invention to provide a sensor sub-unit in the analyzer, positioned in a circular arrangement to form plates of a capacitor, having a plurality of electrode ring pairs coupled to a plurality of timers for converting a capacitance measurement to a frequency and subsequently to identify the levels of FOG, water, sludge and air from the collection of frequencies from the sensor sub-unit.

It is a further object of this invention to provide an interceptor level measurement in real time from an analyzer to a food service establishment to minimize the need for opening and servicing grease interceptors, along with reducing the cost of maintaining them.

It is a further object of this invention to provide a grease interceptor level analyzer having a sensor sub-unit and a controller with a microprocessor having an algorithm for determining more accurate identity of materials and levels of FOG, water, sludge, and air in the interceptor using a calibration of the probe in water and in air.

It is another object of this invention to provide a daisy chain arrangement of the sensor sub-units in the analyzer for performing capacitance measurement of FOG, water, sludge and air levels in interceptors of various heights.

These and other objects are accomplished by an analyzer for measuring identity of materials and levels of fats, oils, grease (FOG), water, sludge and air in an interceptor, the analyzer comprising a probe having an enclosure with a first portion and a second portion, the second portion being secured within the enclosure, the first portion of the probe comprises control means and communication means, the second portion of the probe comprises at least one sensor sub-unit for measuring the levels and identity of FOG, water, sludge and air in the interceptor, and the sensor sub-unit comprises a plurality of electrode ring pairs positioned adjacent to each other, and immediately adjacent to an inside surface of the enclosure, a plurality of timers, each of the timers being coupled to each of the electrode ring pairs respectively in the sensor sub-unit for converting a capacitance measurement of each of the electrode ring pairs to a frequency, a controller, included in the control means of the first portion of the probe, being coupled to each frequency output of each of the plurality of timers and the controller comprises a microprocessor having an algorithm for calculating the frequency output of each of the plurality of timers from a dielectric constant of a medium surrounding the plurality of electrode ring pairs for determining the identity of materials and levels of FOG, water sludge and air in the interceptor. The analyzer having the algorithm in the microprocessor converts the frequency to a value within an arbitrary scale in which zero represents water, 10,000 represents air, and intermediate frequency values represent FOG and sludge. The analyzer comprises a microcontroller in the sensor sub-unit and in response to a signal from the controller enables the capacitance measurements to be made in a sequential manner by each of the timers connected to each of the electrode ring pairs. Each of the electrode ring pairs in the sensor sub-unit comprises two adjacent copper strips sandwiched between sheets of plastic and positioned within a sensor sub-unit in a circular formation forming plates of a capacitor, a dielectric of the capacitor being formed by substances within an influence of an electric field generated by the plates. In their circular configuration the copper strips conform to the inside of the cylindrical pipe that comprises the second portion and is therefore situated as closely as possible to the medium outside the second portion for maximum sensitivity to the medium. The controller comprises means for transmitting the FOG, water, sludge, and air levels and identity of materials to an external receiver. The microprocessor in the controller with the algorithm determines the identity of the materials of FOG, water, sludge or air at each of the electrode ring pairs from arbitrary values within a scale of 0 to 10,000, and the arbitrary values are determined from a calibration of the probe in water and in air in which the frequency of each of the electrode ring pairs is assigned to zero when each of the electrode ring pairs is proximal to water and assigned to 10,000 when each of the electrode ring pairs is proximal to air. The calibration procedure provides four ranges in the scale of 0 to 10,000 which correspond to four components in the interceptor of FOG, water, sludge, and air. A software application of smart devices provides a graphical user interface which combines the four ranges in the 0 to 10,000 scale and presents the frequency, interprets the plurality of electrode ring pairs, and a temperature of the sensor sub-unit.

The objects are further accomplished by a fixed probe when inserted into the interceptor, and communicates the FOG, water, sludge and air levels via a low frequency radio signal to a receiver. The analyzer comprises a portable probe for temporary insertion into the interceptor, and the portable probe communicates the FOG, water, sludge and air levels and identity of materials via Bluetooth® LE to an external device including a phone, tablet or computer hosting a software application written for both iOS and Android devices. The probe is a fixed probe when inserted into the interceptor for continuous monitoring of the materials and levels of the materials in the interceptor, and the fixed probe communicates via LoRa to a gateway that connects via a cellular protocol to a web portal for continuous monitoring of the materials and levels from a remote location. A length of the probe is determined by the length of a single sub-unit or by a number of the sub-units daisy chained, one adjacent to another, each of the sub-units comprises a plurality of the electrode ring pairs coupled to a plurality of the timers and including a microcontroller for enabling the capacitance measurement converted to a frequency by each of the timers in a sequential manner.

The objects are further accomplished by a sensor sub-unit of the analyzer for measuring levels of fats, oils, grease (FOG) water, sludge and air in the interceptor comprising a plurality of electrodes positioned adjacent to each other in a circular arrangement, terminals of the electrodes are attached to the interconnecting circuitry such as a printed circuit board (PCB) and positioned within the circular arrangement of the electrodes, a plurality of timers are positioned on the interconnecting circuitry such as a printed circuit board (PCB), each of the timers receives an input from one pair of the plurality of electrodes forming a plurality of electrode ring pairs, and the plurality of timers convert a capacitance measurement at each of the plurality of electrode ring pairs to a frequency. Each end of the sensor sub-unit comprises a means for connecting sensor sub-units in a daisy chain arrangement, one sub-unit connected to an adjacent sub-unit for enabling the capacitor measurement to be made in interceptors of varying heights. The electrodes comprise metallic electrodes. A microcontroller enables a readout of a capacitance measurement converted to frequency sequentially from an output of each the plurality of timers. A controller receives the capacitance measurement from each of the plurality of timers and determines an identity of materials and the levels of FOG, water, sludge, and air in the interceptor.

The objects are further accomplished by a method for measuring identity of materials and levels of fats, oils, grease (FOG), water, sludge and air in an interceptor, the method comprising the steps of providing a probe having an enclosure with a first portion and a second portion, the second portion being secured within the enclosure, providing a probe having a first portion which comprises control means and communication means, providing a second portion of the probe having at least one sensor sub-unit for measuring the levels and identity of FOG, water, sludge and air in the interceptor, positioning in the sensor sub-unit a plurality of electrode ring pairs positioned adjacent to each other in a circular arrangement, and immediately adjacent to an inside surface of the enclosure, providing a plurality of timers, each of the timers being coupled to each of the plurality of electrode ring pairs respectively in the sensor sub-unit, converting a capacitance measurement of each of the electrode ring pairs to a frequency using a plurality of timers, each of the timers being coupled to each of the plurality of electrode ring pairs respectively in the sensor sub-units, providing a controller in the control means of the first portion of the probe, the controller being coupled to each frequency output of each of the plurality of timers, and determining the identity of materials and levels of FOG, water sludge and air in the interceptor using the controller which includes a microprocessor having an algorithm for calculating the frequency output of each of the plurality of timers from a dielectric constant of a medium surrounding the plurality of electrode ring pairs. The method comprises the step of the algorithm in the microprocessor converting the frequency to a value within an arbitrary scale in which zero represents water, 10,000 represents air and intermediate frequency values represent FOG and sludge. The step of providing a microcontroller in the sensor sub-unit, in response to a signal from said controller, enables the capacitance measurements to be made in a sequential manner by each of the timers connected to each of the electrode ring pairs respectively. The method comprises the step of forming plates of a capacitor positioned within a sensor sub-unit in a circular formation by providing each of the electrode ring pairs with two adjacent copper strips sandwiched between sheets of plastic, a dielectric of the capacitor being formed by substances within an influence of an electric field generated by the plates. The method comprises the step of providing the controller to determine an identity of materials and levels of the FOG, water, sludge, and air in the interceptor, and transmitting the identity of materials and levels to an external receiver. The method further comprises the step of determining the identity of the materials and levels including FOG, water, sludge, and air at each of the electrode ring pairs from a value within the scale of 0 to 10,000, the value being determined from the calibration of the probe in water and in air in which the frequency of each electrode ring pair is assigned to zero when the electrode ring pair is proximal to water and assigned to 10,000 when the electrode ring pair is proximal to air. The method comprises the step of providing the probe as a fixed probe when inserted into the interceptor, and communicating the FOG, water, sludge, and air levels and identity via a low frequency radio signal to a receiver. The method comprises the step of providing a portable probe for temporary insertion into the interceptor and communicating the FOG, water, sludge, and air levels and identity via Bluetooth® LE to an external device including a phone, tablet, or computer hosting a software application written for both iOS and Android devices. The method comprises the step of providing a fixed probe within the interceptor for continuous monitoring of the materials and levels, and communicating via LoRa to a gateway that connects via a cellular protocol to a web portal for the continuous monitoring of the materials and levels from a remote location. The method comprises the step of determining a length of the probe by the number of the sub-units daisy chained, one adjacent to another, each of the sub-units comprising a plurality of the electrode ring pairs coupled to a plurality of the timers and including a microcontroller for enabling the capacitance measurement converted to a frequency by each of the timers in a sequential manner.

BRIEF DESCRIPTION OF THE DRAWINGS

The claims particularly point out and distinctly claim the subject matter of this invention. The various objects, advantages, and novel features of this invention will be more fully apparent from a reading of the following detailed description in conjunction with the accompanying drawings in which like reference numerals refer to like parts, and in which:

DETAILED DESCRIPTION OF PREFERRED EMBODIMENTS

Figure 1:
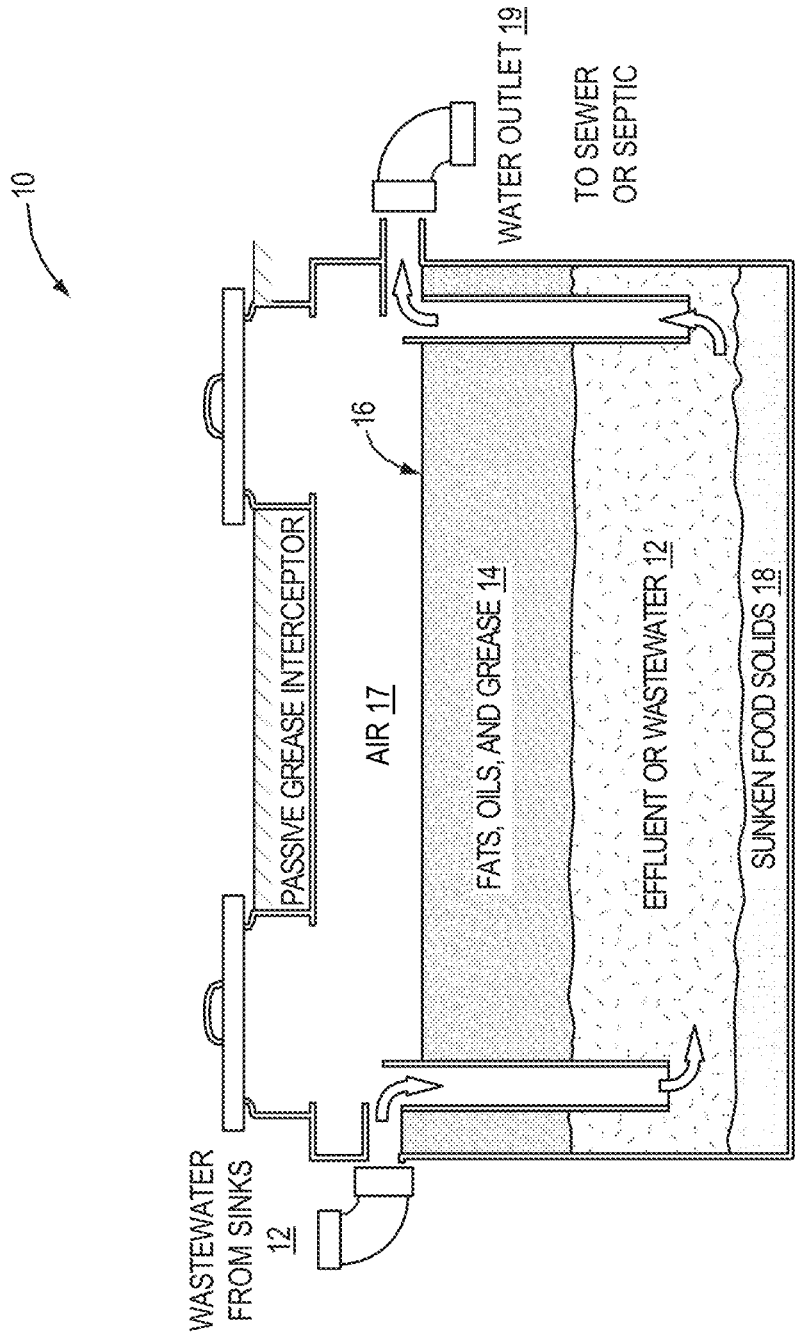
FIG. 1 is a graphic illustration of a prior art grease interceptor tank.
Figure 2:
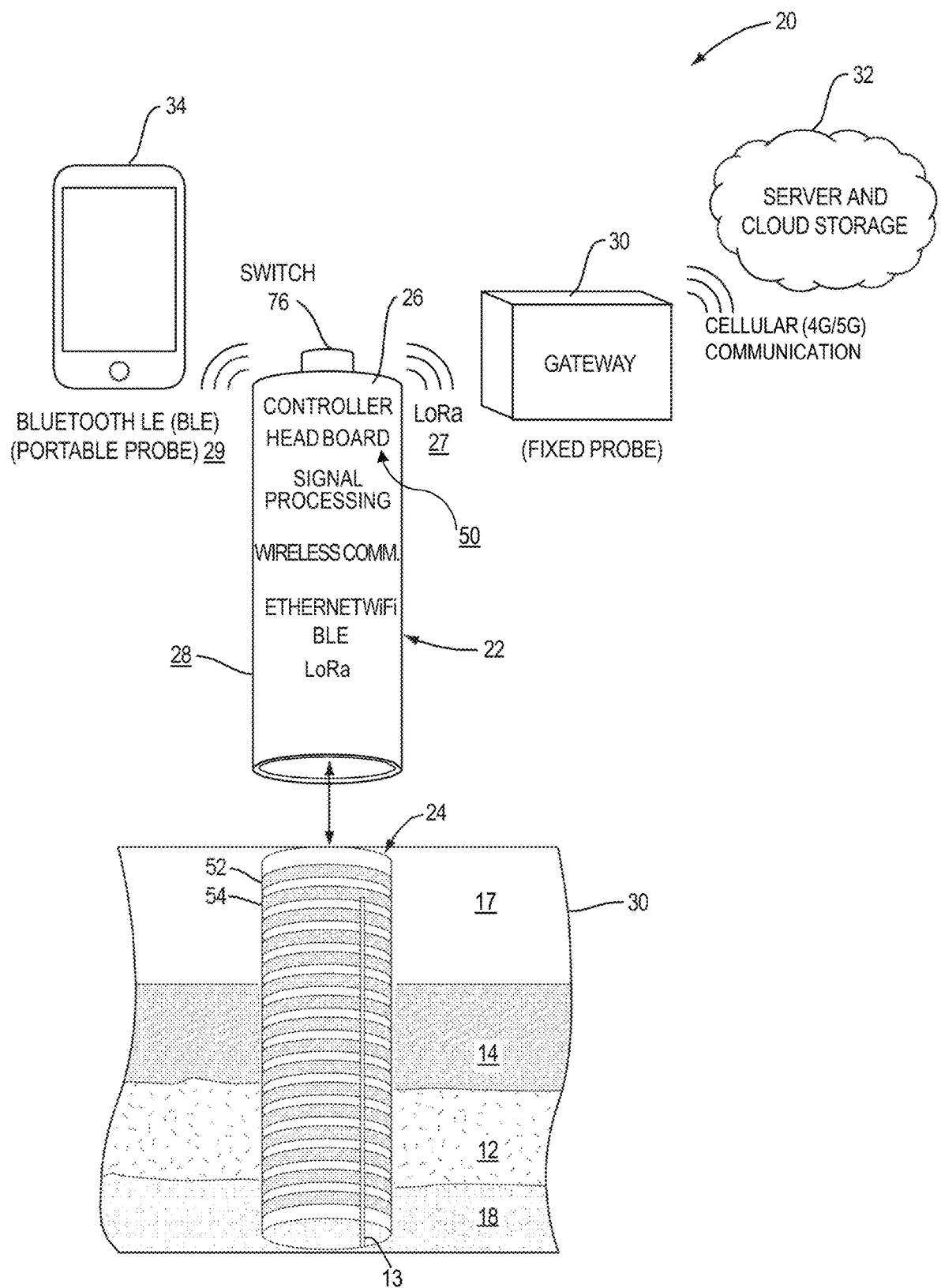
FIG. 2 is a graphic illustration of a grease interceptor level analyzer system according to the present invention.

Referring to FIG. 2, a block diagram of a capacitance-based grease interceptor level analyzer (GILA) system 20 is shown for providing in real time fats, oils, grease (FOG), water, sludge and air levels information in an interceptor 10 to a food service establishment (FSE), to an authority having jurisdiction (AHJ) or to an interceptor service company. The GILA system 20 including a probe 22, a probe sensor sub-unit 24, and a controller 26, is contained within an environmentally sealed container 28 such as a plastic pipe. The controller 26 transmits measurement data to a gateway 31 via low frequency radio signal (LoRa) 27. The gateway 31 transmits data to a server and cloud storage 32. Further, the controller 26 communicates with a smart device 34 such as a cell phone via Bluetooth® LE (BLE) 29, which is a short range wireless technology commonly known in the art.

Still referring to FIG. 2, there are two embodiments of the probe 22, a fixed probe 22 and a portable probe 23. The portable probe 23 communicates via Bluetooth® 29 or short-range wireless technology commonly known in the art to the smart device 34 and displays the levels of FOG, water, sludge and air. It can also send data to the server and cloud storage 32. This embodiment is made principally for municipal inspectors who enforce grease interceptor regulations. For the display and storage of data in a portable probe 23, the user configures the probe 23 through a wireless Bluetooth® Low Energy (BLE) 29 connection. A software application (app) for both Android and iOS smart devices commonly known in the art provides the user interface for configuring and viewing the probe 23 data. The app establishes communication with the probe 23, and provides text fields for the user to describe the probe 23 and/or interceptor 30 being tested and guides the user through calibration.

The fixed probe 22 is permanently enclosed in a grease interceptor 30 (FIG. 2) and communicates, via a low frequency radio signal (LoRa) 27 to a receiver gateway 31 on premises. The receiver gateway 31, in turn, transmits data via cellular communications to the server and cloud-storage service 32. This embodiment is made principally for FSE owners/operators and service companies that pump out the interceptors.

In both embodiments of the probes 22, 23 the enclosure 28 is an environmentally sealed plastic pipe. Inside the probe 22, is a (replaceable) battery, a controller 26, a sensor sub-unit 24 having one or more sensor circuits 40, each mounted on a Printed Circuit Board (PCB) and each connected to a sheet of 8 pairs of electrodes. When inserted into the plastic pipe the sheet of electrodes conforms to the circular geometry of the pipe which increases accuracy of level measurements. In their circular configuration the copper strips conform to the inside of the cylindrical pipe that comprises the second portion and is therefore situated as closely as possible to the medium outside the second portion for maximum sensitivity to the medium. The head board with the controller 26 is different for the two versions while the same sensor circuits 40 are used for both.

In FIG. 2, the GILA probe 22 makes periodic capacitance measurements to determine the levels of FOG, water, sludge and air in a grease interceptor 30. The default period time is 15 minutes though the user can change the frequency of readings. The fixed probe 22 is powered by a battery so there is a trade-off between frequency of readings and battery lifetime. At a 15-minute interval between readings, the battery lifetime is approximately one year.

Figure 3:
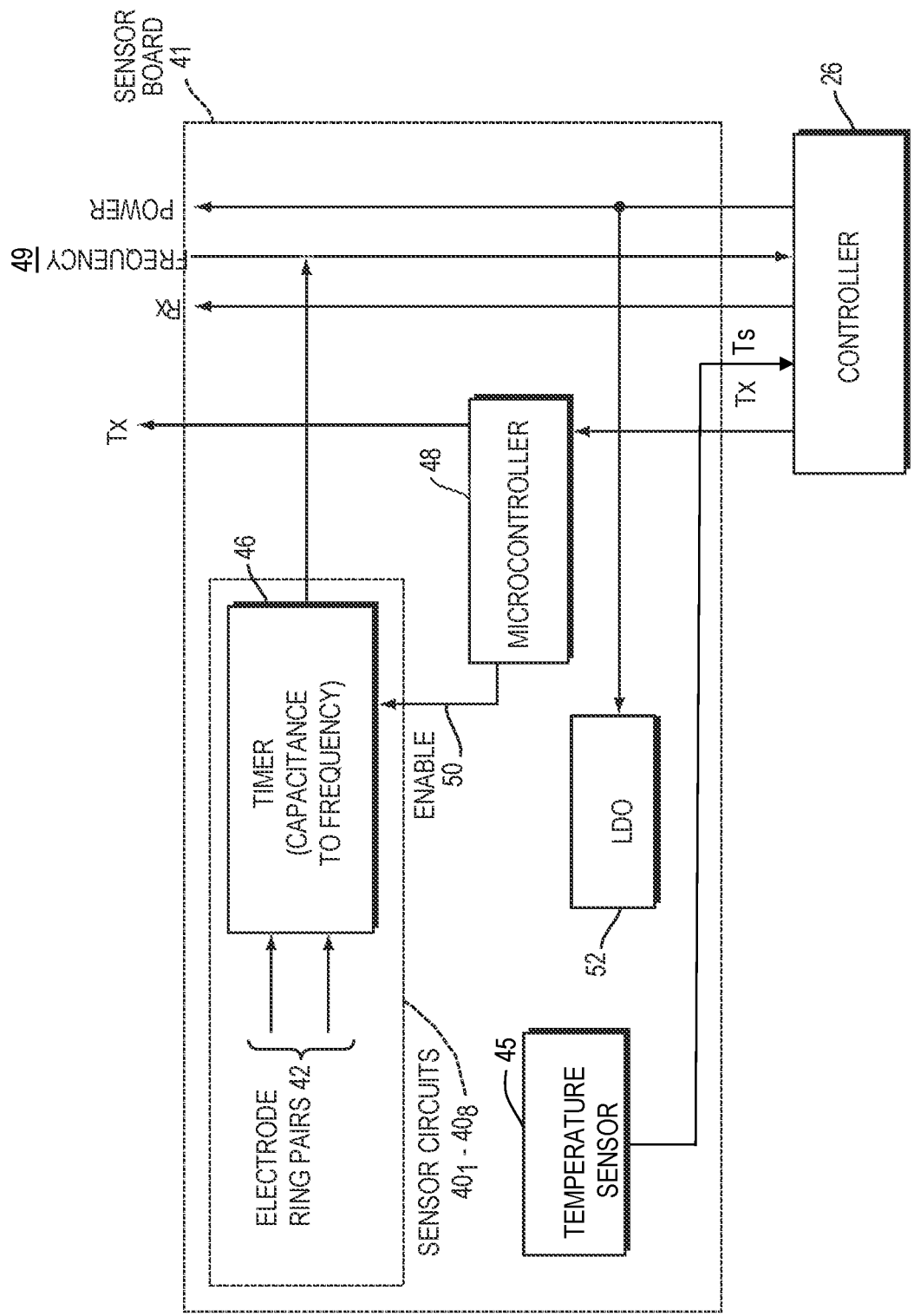
FIG. 3 is a block diagram of capacitance measurement sensor circuits.
Figure 8:
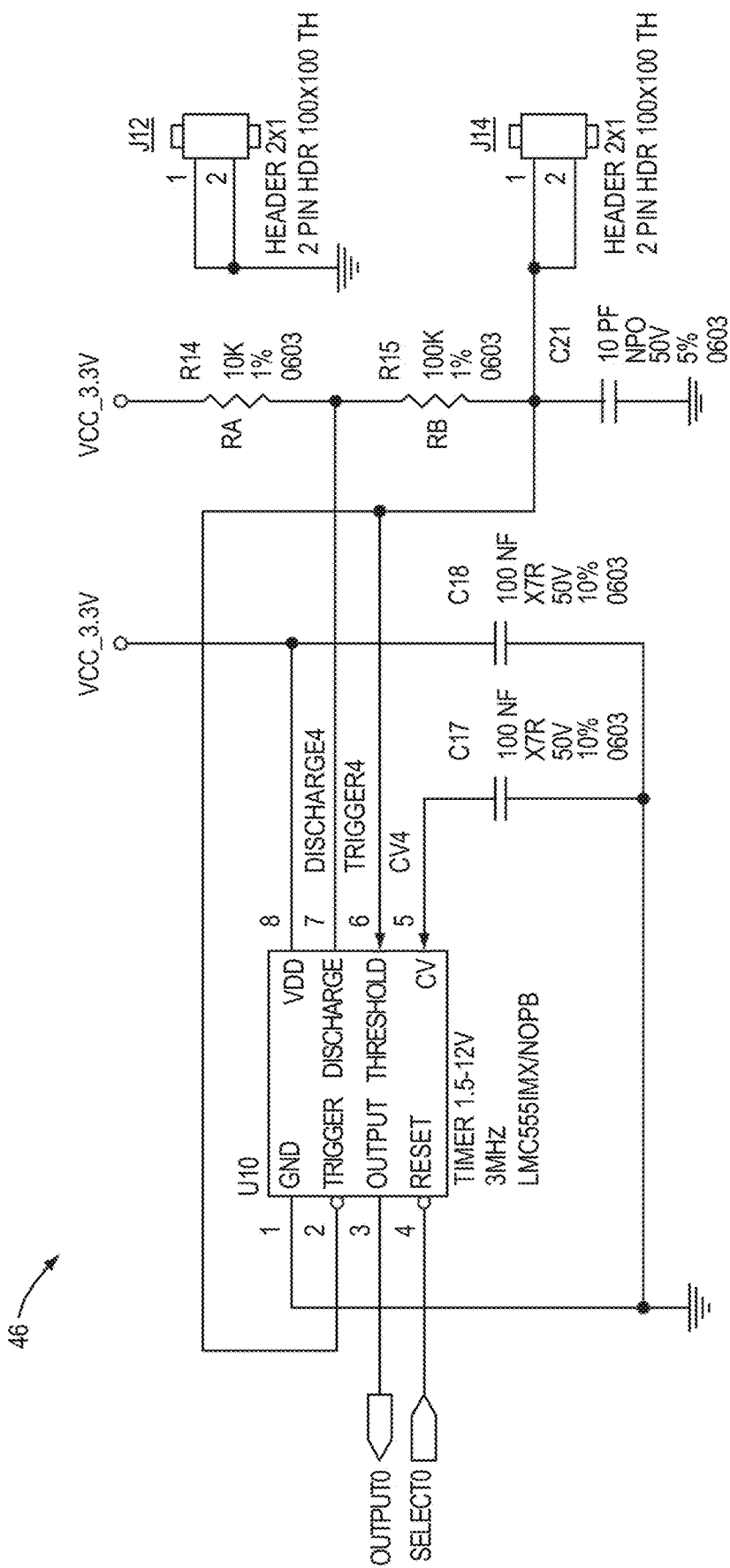
FIG. 8 is a schematic diagram of the timer circuit in the sensor circuit of FIG. 3.

Referring to FIG. 3, a block diagram of sensor circuits $40_1$ to $40_8$ in the probe 22 is shown. There are eight pairs of electrodes 42 connected to eight timer circuits $46_1$ to $46_8$ that convert capacitance to frequency, and the eight timer circuits 46 are sequentially activated by a microcontroller 48 enable 50 output. As shown in FIG. 8, a schematic of the timer 46 is provided which measures the capacitance of one of the copper electrode ring pairs 42. There is a timer 46 for each sensor circuit $40_1$-$40_8$ as shown in FIG. 3. The timer $46_1$ to $46_8$ may be embodied by part no. LMC5551MX/NOPB well known in the art (See FIG. 8). The microcontroller 48 may be embodied by Microchip part no. ATTINY828R-AURCT, commonly known in the art. The LDO 52 is a low drop out voltage regulator, commonly known in the art.

Figure 5:
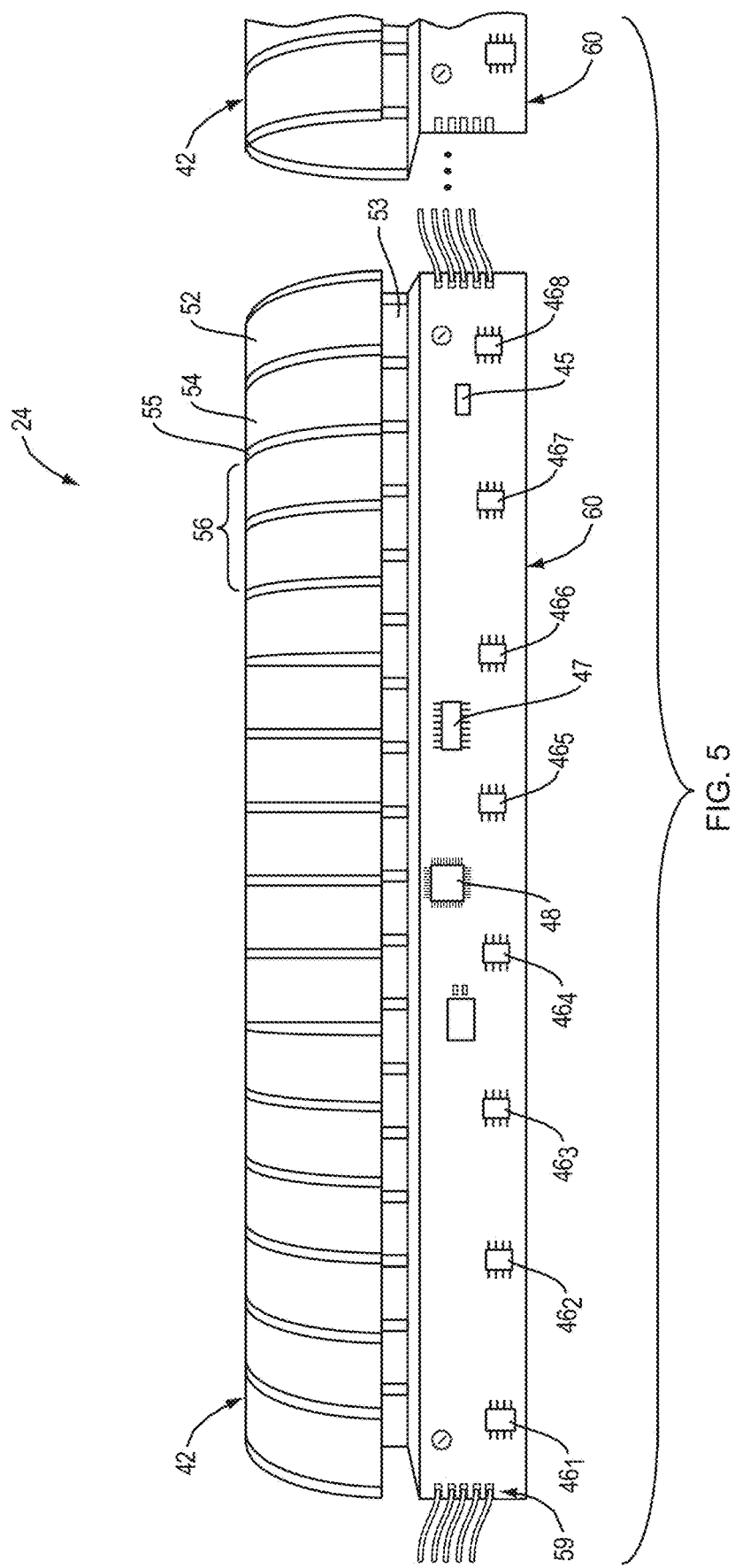
FIG. 5 is a graphic cutaway illustration of a probe sensor sub-unit with eight pairs of circular sensor electrodes partially opened to show the sensor circuits printed circuit board.

The output of each sensor circuit $40_1$ to $40_8$ is a square wave clock signal with a frequency that is proportional to the capacitance of each of the electrode ring pairs 42. The timer 46 operates in an astable configuration as shown in FIG. 8. A supply voltage Vcc of 3.3V causes the timer to switch between high and low at a frequency that is proportional to the capacitance: $f=1.44/[(R1+R2) \times C]$. The outputs of all sensor circuits $40_1$ to $40_8$, each on a small circuit board, are wired to a frequency bus 49 that runs along the multiple sensor circuits $40_1$-$40_8$ on the PCB 60 (FIG. 5). Only one of the electrode ring pairs 42 is enabled at a time by the microcontroller 48 to provide a frequency output from each timer 46.

The assembly of eight electrode ring pairs 42, the PCB 60 containing the timers $46_1$-$46_8$, and a microcontroller 48 comprise primarily one sensor sub-unit 24 of the probe 22. Several sensor sub-units 24 can be daisy chained, one adjacent to another, to extend the length of the probe 22 in increments of approximately 8 inches for use in varying heights of interceptors 30. When the sub-unit 24 is the lower unit in a daisy chain configuration as illustrated in FIG. 5, there would be no connections to the terminals 59 in FIG. 5. For example, four sub-units 24 with four PC boards 60 (FIG. 5) containing a total of 32 sensor circuits 40 make a probe 22 that will measure an interceptor 30 approximately 32 inches high.

Figure 6:
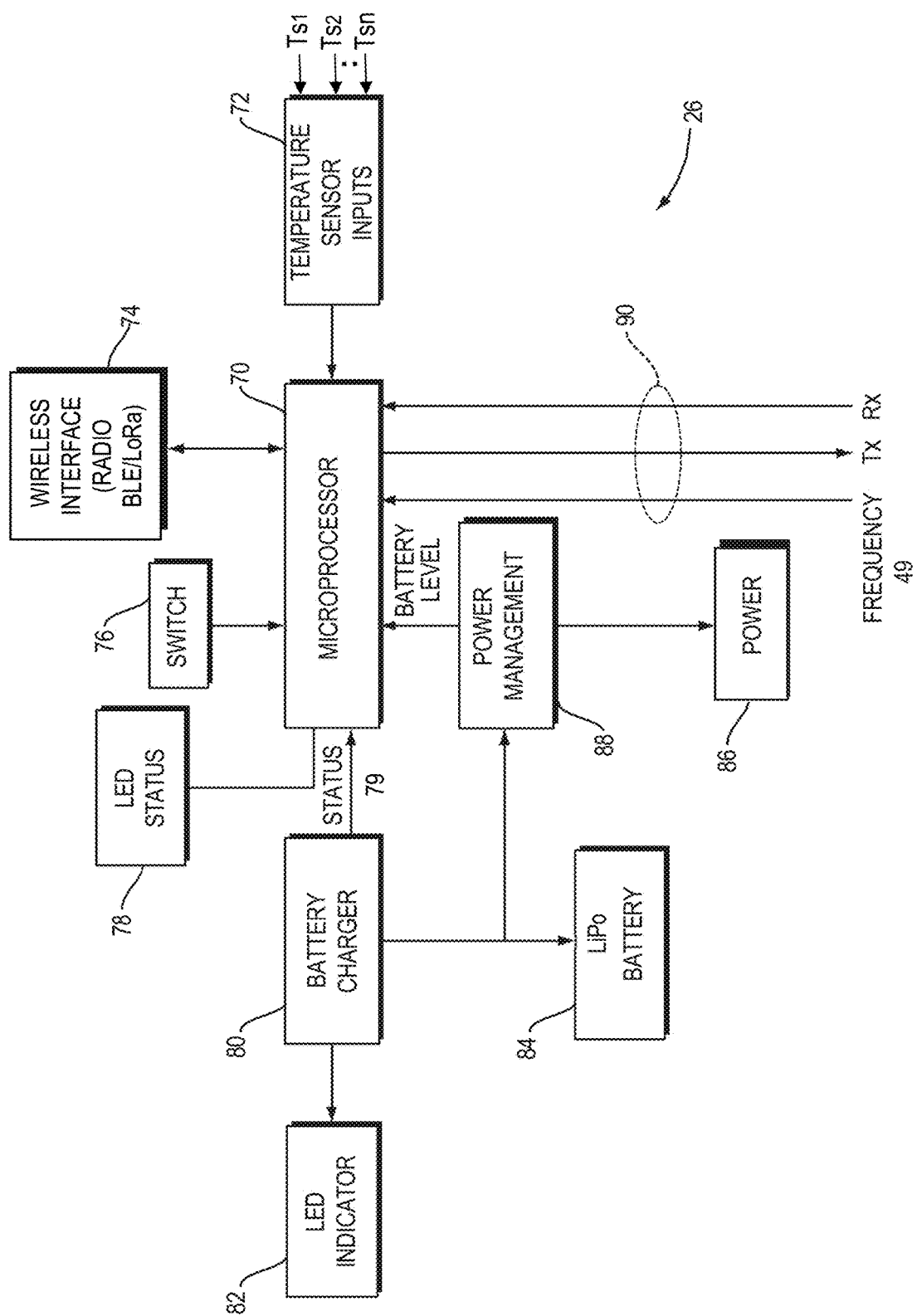
FIG. 6 is a block diagram of a probe controller.

The microcontroller 48 connected to the sensor circuits $40_1$-$40_8$, outputs each of the sensor frequency values in a sequential manner as directed by the controller 26 (FIG. 6). The controller 26 collects the frequencies generated by their timer circuits $46_1$-$46_8$ and stores the results. The key point is that the microcontroller 48 for the eight sensor circuits $40_1$-$40_8$ controls the readout of the timer $46_1$-$46_8$ operating in an astable mode. In this mode the timer 46 outputs a frequency that is proportional to the capacitance of the electrode ring pairs 42 formed by the eight parallel copper rings 56 (FIG. 4) that senses the interceptor 30 medium.

There are two lines of communication between the sensor circuits $40_1$-$40_8$ and the controller 26 (see FIG. 6). The Status Line $T_x$ initiates and terminates the capacitance measurement. The two values for the Status Line are LOW and HIGH. The Frequency Line 49 transmits the capacitance measurement to the controller 26 for storage and identity of the various levels within the interceptor 30.

The probe 22 includes a number of sensor-based printed circuit board (PCB) elements. Each sensor circuit $40_1$-$40_8$ PCB comprises the timers 46, and common electronic components, i.e. resistors, capacitors, buffers and LED's). The microcontroller 48 controls all switching and timing functions of the sensor circuits $40_1$-$40_8$.

Figure 4:
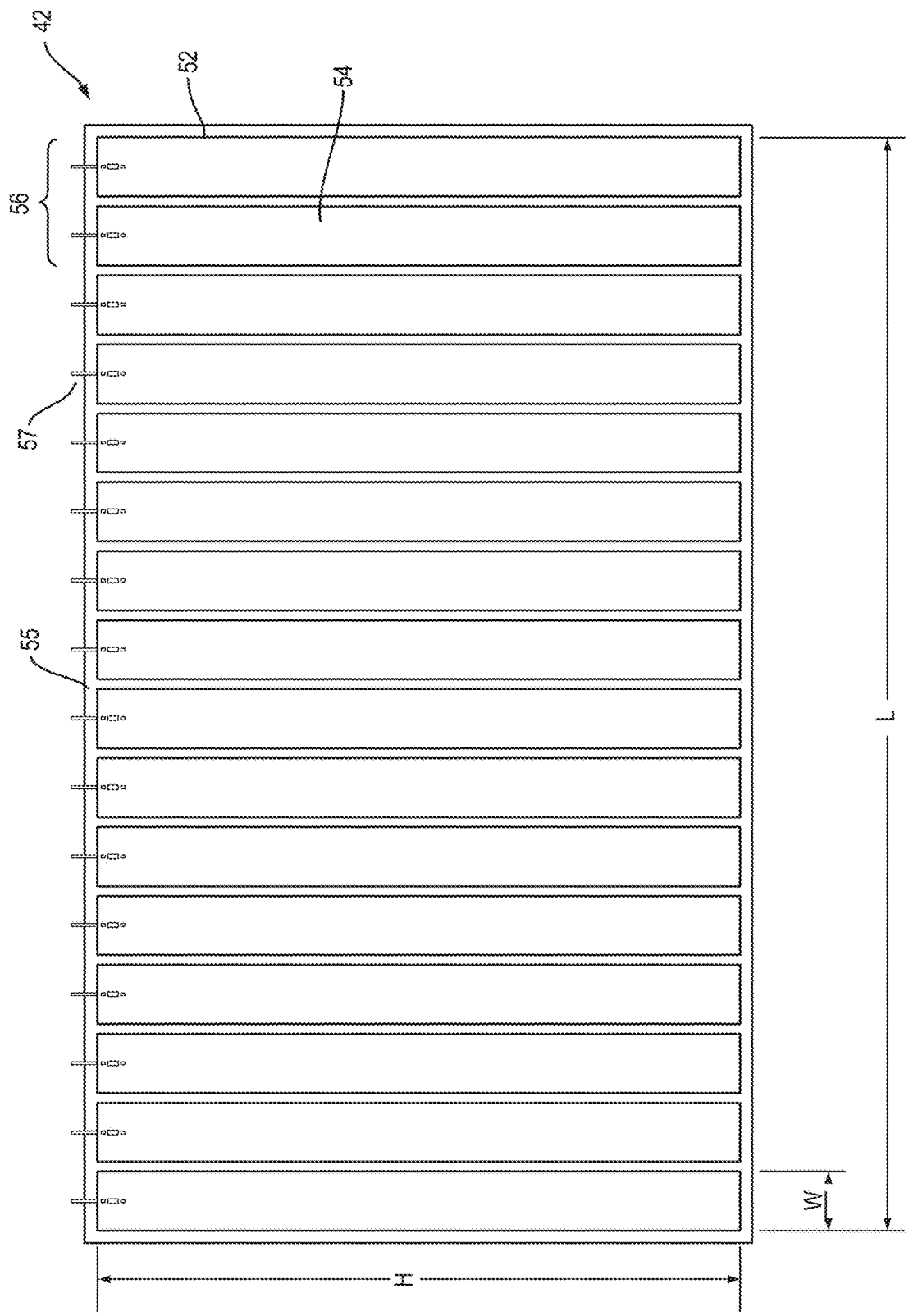
FIG. 4 is a schematic diagram of adjacent copper strips embedded in plastic used to form sensor electrodes of a sensor sub-unit.

Referring now to FIG. 4, a schematic of adjacent copper strips that form sensor electrodes 42 as shown for a sensor sub-unit 24 (FIG. 5) of the probe 22. Two adjacent copper strips 52 and 54, are embedded in plastic 55 and constitute one electrode pair 56. Eight pairs of electrodes 56 are provided in one sensor sub-unit 24. The array of 16 copper strips forming electrode ring pairs 42, has typical dimensions of height (H) 4.7 inches, width (W) 0.5 inches of the copper strip, and the array length (L) 8.0 inches.

As described above, there is one dedicated sensor circuit 40 for each capacitance measurement. Each sensor circuit $40_1$-$40_8$ contains a capacitor in the form of two parallel, thin copper electrodes 52 and 54 in a circular formation (FIG. 5). Capacitance values are made relative to water. Eight pairs of electrodes 56, spaced adjacent to each other, form eight electrode ring pairs 42 in one sensor sub-unit 24. The eight pairs of electrodes 56 are spaced at approximately one inch along the length of the probe 22. The entire array of eight pairs of thin copper strip electrodes 56 are sandwiched between two sheets of clear plastic 55.

FIG. 4 shows the array of eight pairs of electrodes 56. Each copper strip 52 has a terminal 57, for connections, to the timer 46 circuit. The timer circuits $46_1$-$46_8$, each sequentially controlled by the microcontroller 48, are mounted on a printed circuit board 60 and connect to the sensor electrode ring pairs 42.

Referring to FIG. 5, a sensor sub-unit 24 of probe 22, comprises printed circuit board (PCB) 60 positioned within the circular sensor electrode ring pairs 42 which are opened up or cut away for illustration purposes in FIG. 5 to show the PCB 60 inside the plurality of rings of electrodes 56. The microcontroller 48 can be seen in the center of the PCB 60. The PCB 60 attaches to a backbone 13 (FIG. 2) along with sensor sheets 55. Each of the eight timer circuits $46_1$ to $46_8$ connect to one pair of electrodes 56 located above the timer circuits. The pair of electrode rings 56 are constructed from thin copper strips 52 sandwiched between sheets of plastic 55 as shown in FIG. 4. When inserted into the enclosure 28 (plastic pipe), the flexible sensor sub-unit 24 conforms to the interior of the enclosure 28. As previously described any number of these sensor sub-units 24 can be connected together to create a probe 22 that is a multiple of eight sensor electrode ring pairs 42. The microprocessor 70 (FIG. 6) in the controller 26 activates the microcontroller 48 of each sub-unit 24 sequentially. Each microcontroller 48 enables each pair of electrodes 56 and measures the electrode pair capacitance via the timer 46, which converts capacitance to a frequency. The result is that the microprocessor 70 in the controller 26 (FIG. 6) initiates the reading of capacitance of every pair of electrodes 56 from top to bottom in the probe 22 or 23, and determines whether the contents at each pair of electrodes 56 is FOG, water, sludge or air. The proximity of the electrodes 56 against the surface of the probe 22 maximizes the electric field in the interceptor interior and increases the precision of the capacitance measurement.

Referring to FIG. 6, a block diagram of the controller 26 is shown. The controller 26 provides the following three main functions for the probe 22: (a) drives the frequency measurement of each sensor circuit $40_1$-$40_8$. (b) determines the identity of materials and levels of the content of an interceptor 30 such as FOG, water, sludge and air of each sensor circuit $40_1$-$40_8$, and (c) transmits the identity of each level through one of three wireless methods. This controller 26 is attached to a printed circuit board which is referred to as the headboard 50 (FIG. 2). The controller 26 comprises a microprocessor 70 and communicates with each of the sensor circuits $40_1$-$40_8$ via a serial bus interface 90. The microprocessor 70 is programmed to instruct the microcontroller 48 in each sensor circuit 40 to send an Enable signal 50 to generate the frequency 49 output. The controller 26 communicates the results of the interpreted frequency measurements to the wireless interface 74. The portable probe 23 uses Bluetooth® low energy (BLE) 29 and the fixed probe 22 uses the low radio frequency protocol LoRa 27. The wireless interface 74 is also used for control, configuration, and firmware updates.

Still referring to FIG. 6 an external switch 76 turns the controller 26, and therefore the probe 22 or 23, ON and OFF. The temperature sensor inputs 72 provide a temperature reading of the interceptor 30 environment. The LED 78 provides status information to a user. The LED indicator 82 provides a voltage reading of the LiPo battery 84 and the battery charger 80 is controllable by the microprocessor 70 and power management circuit 88, and the power 86 provides voltages to the sensor circuits $40_1$-$40_8$. The microprocessor 70 may be embodied by part number ESP32 by Esprssif, commonly known in the art.

For determining the fluid or material type in an interceptor 30, the capacitance of each sensor circuits $40_1$-$40_8$ or materials as represented by a frequency value is mapped to the identity of the fluid or materials at the sensor electrode ring pairs 42 as being either FOG, water, sludge or air. A lookup table, constructed through laboratory testing, determines the range of frequencies appropriate for each type of fluid or material. For differentiating more accurately between sludge and water or between FOG and air, both pairs of fluids having very similar capacitance values, an algorithm based on the derivative of frequency values is used. The algorithm converts the frequency value of each sensor circuit 40 into an arbitrary number, such that the frequency maps to 0 when the sensor is proximal to water and maps to 10,000 when the electrode is proximal to air. A calibration procedure directs the user to immerse the probe, first in water and second in air. This calibration procedure accomplishes two objectives: first, it converts the range frequency values from the multiple sensors to the arbitrary scale of 0 to 10,000; second, it minimizes the discrepancy of frequency output values amongst the plurality of sensor circuits 40 in the probe, thus ensuring a more accurate reading. The values for sensor circuits 40, when proximal to FOG, range from approximately 1000 to 2000. The user assigns the four ranges of arbitrary values related to the four possible identities of material, i.e. water 12, sludge 18, FOG 14, and air 17. The user interface for configuring these ranges as well as viewing sensor circuits 40 outputs is via a graphical user interface embodied in a software application ("app") of a smart mobile device 34, when using the probe 23 in its portable configuration, or a cloud 32 based portal when using the probe 22 in its fixed configuration.

The probe data is embodied in a bar graph on the smart device 34 that is divided into horizontal segments. Each segment corresponds to one sensor circuit 40 and is color coded to represent the identity of the material at that level including FOG, water, sludge or air. Other data provided includes frequency values for the plurality of sensor circuits 40, the scaled values of the 0 to 10,000 range associated with the measured frequencies, the identity of the material (FOG, water, sludge, or air) proximal to each sensor based on the scaled value and its assignment, and the temperature of each sensor sub-unit 24 as measured by a temperature sensor 45 mounted to each sensor sub-unit printed circuit board 60. The total volume of the interceptor 30 contents of FOG and sludge is expressed as a fraction of the interceptor 30 contents. Many Authorities Having Jurisdiction (AHJ) mandate that this fraction be no greater than 25%.

For the display and storage of data in a fixed probe 22, the headboard of the controller 26 of a fixed probe 22 also contains a radio that transmits data via the LoRa 27. The radio communicates to a transmitter gateway 30 mounted in the vicinity of the grease interceptor, e.g. on a wall or in an office. The transmitter relays the data to a server and cloud 32 file via cellular communication.

Figure 7:
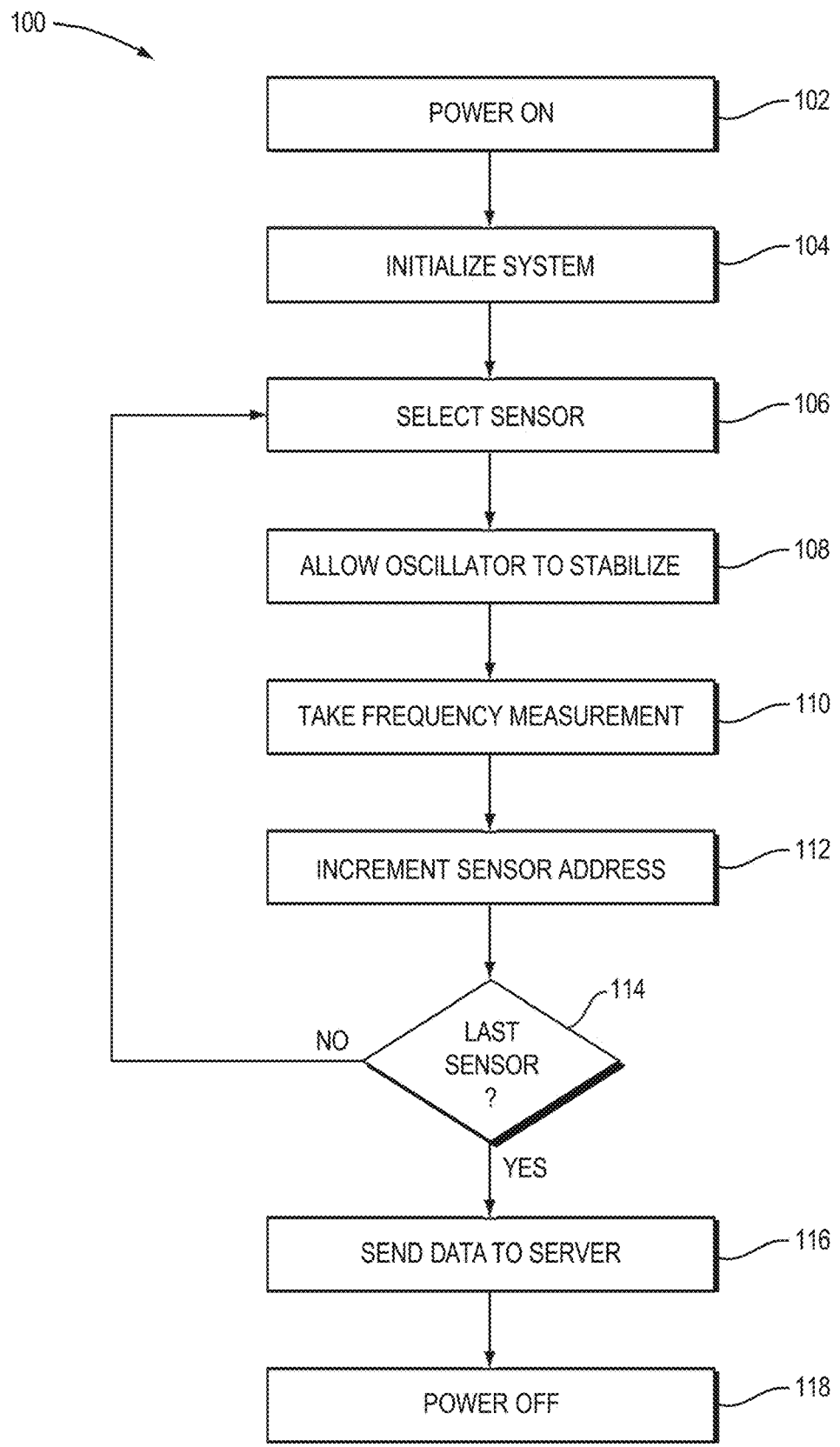
FIG. 7 is a flow chart of the method of FOG probe capacitance measurement sequence of operation according to the present invention.

Referring to FIG. 7, the steps of the method 100 of capacitance measurements are as follows: Prior to a measurement all sensor circuits $40_1$-$40_8$ are powered OFF and in Step 102 power is turned ON. In Step 104 the microprocessor 70 initializes the system.

In Step 106 the selection of a sensor circuit $40_1$-$40_8$ is made. The status line switches to HIGH for 1 millisecond (ms) then LOW for 1 ms and then stays HIGH. In Step 108 oscillations are allowed to stabilize.

In Step 110 the frequency measurement is made as follows: The microcontroller 48 (FIG. 3) switches the connection to the timer circuit for 4 seconds. This timer 46 outputs a square wave on the frequency line 49. The status line 79 switches to LOW for 1 ms then switches HIGH. This signals that the frequency of the sampling capacitor is to be measured. The microcontroller 48 switches the connection between the sampling capacitor and timer 46 for 4 seconds. This outputs a square wave on the frequency line 49. The frequency of the square wave is proportional to the sample capacitance. The microprocessor 70 adds the values of the frequency to a record.

In Step 112 the sensor circuit 40 address is incremented, and in Step 114 it is determined if there is another sensor circuit, and if so the operation returns to Step 106. Otherwise, the operation goes to Step 116 and the measured data is sent to the server 39, and in Step 118 power is turned OFF. If the operation is returned to Step 106, then a second measurement is made and the values added to the record. The microprocessor 70 continues this loop of Steps 106 to 114 until the microprocessor 70 cannot find the next sensor circuit $40_1$-$40_8$ at which point it completes the record and transmits the data to the controller 26.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An analyzer for measuring identity of materials and levels of fats, oils, grease (FOG), water, sludge and air in an interceptor, said analyzer comprising:
a probe having an enclosure with a first portion and a second portion, said second portion being secured within said enclosure;
said first portion of said probe comprises control means and communication means;
said second portion of said probe comprises at least one sensor sub-unit for measuring said levels and identity of FOG, water, sludge and air in said interceptor;
said sensor sub-unit comprises a plurality of electrode ring pairs positioned adjacent to each other, and immediately adjacent to an inside surface of said enclosure;
a plurality of timers, each of said timers being coupled to each of said electrode ring pairs respectively in said sensor sub-unit for converting a capacitance measurement of each of said electrode ring pairs to a frequency;
a controller, included in said control means of said first portion of said probe, being coupled to each frequency output of each of said plurality of timers; and
said controller comprises a microprocessor having an algorithm for calculating said frequency output of each of said plurality of timers from a dielectric constant of a medium surrounding said plurality of electrode ring pairs for determining said identity of materials and levels of FOG, water sludge and air in said interceptor.

2. The analyzer as recited in claim 1 wherein said algorithm in said microprocessor converts said frequency to a value within an arbitrary scale in which zero represents water, 10,000 represents air and intermediate frequency values represent FOG and sludge.

3. The analyzer as recited in claim 1 wherein a microcontroller in said sensor sub-unit and in response to a signal from said controller enables said capacitance measurements to be made in a sequential manner by each of said timers connected to each of said electrode ring pairs.

4. The analyzer as recited in claim 1 wherein each of said electrode ring pairs comprises two adjacent copper strips sandwiched between sheets of plastic and positioned within a sensor sub-unit in a circular formation forming plates of a capacitor, a dielectric of said capacitor being formed by substances within an influence of an electric field generated by said plates.

5. The analyzer as recited in claim 1 wherein said controller comprises means for transmitting said FOG, water, sludge, and air levels and identity of materials to an external receiver.

6. The analyzer as recited in claim 1 wherein said algorithm determines the identity of the materials including FOG, water, sludge or air at each of said electrode ring pairs from arbitrary values within a scale of 0 to 10,000, said arbitrary values being determined from a calibration of said probe in water and in air in which the frequency of each of said electrode ring pairs is assigned to zero when each of the electrode ring pairs is proximal to water and assigned to 10,000 when each of said electrode ring pairs is proximal to air.

7. The analyzer as recited in claim 6 wherein said calibration procedure provides four ranges in said scale of 0 to 10,000 which corresponds to component materials in said interceptor of FOG, water, sludge, and air.

8. The analyzer as recited in claim 7, wherein a software application of smart devices provides a graphical user interface which combines said four ranges in said 0 to 10,000 scale and presents said frequency interprets said plurality of electrode ring pairs and a temperature of said sensor sub-unit.

9. The analyzer as recited in claim 1 wherein said probe comprises a fixed probe when inserted into said interceptor, and communicates said FOG, water, sludge and air levels via a low frequency radio signal to a receiver.

10. The analyzer as recited in claim 1 wherein said probe comprises a portable probe for temporary insertion into said interceptor, and said portable probe communicates said FOG, water, sludge and air levels and identity of materials via Bluetooth® LE to an external device including a phone, tablet or computer hosting a software application written for both iOS and Android devices.

11. The analyzer as recited in claim 1 wherein said probe is a fixed probe when inserted into said interceptor for continuous monitoring of said materials and levels of said materials in said interceptor, and said fixed probe communicates via LoRa to a gateway that connects via a cellular protocol to a web portal for continuous monitoring of said materials and levels from a remote location.

12. The analyzer as recited in claim 1 wherein a length of said probe is determined by the length of a single or by a number of said sub-units daisy chained, one adjacent to another, each of said sub-units comprises a plurality of said electrode ring pairs coupled to a plurality of said timers and including a microcontroller for enabling said capacitance measurement converted to a frequency by each of said timers in a sequential manner.

13. A sensor sub-unit of an analyzer for measuring levels and identity of fats, oils, grease (FOG), water, sludge and air in an interceptor comprising:

a plurality of electrodes positioned adjacent to each other in a circular arrangement;

terminals of said electrodes are attached to interconnecting circuitry and positioned within said circular arrangement of said electrodes;

a plurality of timers positioned on said interconnecting circuitry, each of said timers receives an input from one pair of said plurality of electrodes forming a plurality of electrode ring pairs;

said plurality of timers convert a capacitance measurement at each of said plurality of electrode ring pairs to a frequency, said frequency being processed by an algorithm for converting said frequency of each of said plurality of timers to a value within an arbitrary scale in which 0 represents water, 10,000 represents air, and intermediate converted frequency values represent said fog and sludge; and each end of said sub-unit comprises a means for connecting said sensor sub-unit in a daisy chain arrangement, one sub-unit connected to an adjacent sub-unit, for enabling said capacitor measurement to be made in said interceptor of varying heights.

14. The sensor sub-unit as recited in claim 13 wherein said electrodes comprise metallic electrodes.

15. The sensor sub-unit as recited in claim 13 wherein a microcontroller enables a readout of a capacitance measurement converted to frequency sequentially from an output of each of said plurality of timers.

16. The sensor sub-unit as recited in claim 15 wherein a controller receives said capacitance measurement converted to frequency from each of said plurality of timers and determines an identity of materials and levels of said FOG, water, sludge, and air in said interceptor.

17. The sensor sub-unit as recited in claim 13 wherein said means for interconnecting components and circuits comprises a printed circuit board (PCB).

18. A sensor sub-unit of an analyzer for measuring levels and identity of fats, oils, grease (FOG), water, sludge, and air in an interceptor comprising:

a plurality of electrodes positioned adjacent to each other in a circular arrangement;

terminals of said electrodes are attached to means for interconnecting components and circuits and positioned within said circular arrangement of electrodes;

a plurality of timers positioned on said interconnecting means, each of said timers receives an input from one pair of said plurality of electrodes forming a plurality of electrode ring pairs;

said plurality of timers convert a capacitance measurement at each of said plurality of electrode ring pairs to a frequency, said frequency being processed by an algorithm for converting said frequency of each of said plurality of timers to a value within an arbitrary scale in which 0 represents water, 10,000 represents air, and intermediate converted frequency values represent said fog and sludge;

a microcontroller enables a readout of said capacitance measurement converted to frequency sequentially from an output of said plurality of timers; and said sensor sub-unit comprises an enclosure wherein said electrode ring pairs are positioned within said sensor sub-unit immediately adjacent to an inside surface of said enclosure.

19. The sensor sub-unit as recited in claim 18 wherein a controller within said enclosure receives said capacitance measurement converted to a frequency from each of said plurality of timers and determines an identity of materials of said levels of FOG, water, sludge, and air in said interceptor.

20. The sensor sub-unit as recited in claim 18 wherein said means for interconnecting components and circuits comprises a printed circuit board.

21. A method for measuring identity of materials and levels of fats, oils, grease (FOG), water, sludge and air in an interceptor, said method comprising the steps of:

providing a probe having an enclosure with a first portion and a second portion, said second portion being secured within said enclosure;

providing a probe having a first portion which comprises control means and communication means;

providing a second portion of said probe having at least one sensor sub-unit for measuring said levels and identity of FOG, water, sludge and air in said interceptor;

positioning in said sensor sub-unit comprises a plurality of electrode ring pairs positioned adjacent to each other in a circular arrangement, and immediately adjacent to an inside surface of said enclosure;

providing a plurality of timers, each of said timers being coupled to each of said plurality of electrode ring pairs respectively in said sensor sub-unit;

converting a capacitance measurement of each of said electrode ring pairs to a frequency using a plurality of timers, each said timer being coupled to each of said plurality of electrode ring pairs respectively in said sensor sub-units;

providing a controller in said control means of said first portion of said probe, said controller being coupled to each frequency output of each of said plurality of timers; and determining said identity of materials and levels of FOG, water sludge and air in said interceptor using said controller, said controller including a microprocessor having an algorithm for calculating said frequency output of each of said plurality of timers from a dielectric constant of a medium surrounding said plurality of electrode ring pairs.

22. The method as recited in claim 21 comprises the step of said algorithm in said microprocessor converting said frequency to a value within an arbitrary scale in which zero represents water, 10,000 represents air and intermediate frequency values represent FOG and sludge.

23. The method as recited in claim 21 comprises the step of providing a microcontroller in said sensor sub-unit, and in response to a signal from said controller, enabling said capacitance measurements to be made in a sequential manner by each of said timers connected to each of said electrode ring pairs respectively.

24. The method as recited in claim 21 comprises the step of forming plates of a capacitor positioned within a sensor sub-unit in a circular formation by providing each of said electrode ring pairs with two adjacent copper strips sandwiched between sheets of plastic, a dielectric of said capacitor being formed by substances within an influence of an electric field generated by said plates.

25. The method as recited in claim 21 comprises the step of providing said controller to determine an identity of materials and levels of said FOG, water, sludge, and air in said interceptor, and transmitting said identity of materials and levels to an external receiver.

26. The method as recited in claim 21 comprises the step of determining the identity of the materials and levels including FOG, water, sludge, and air at each of said electrode ring pairs from a value within the scale of 0 to 10,000, said value being determined from the calibration of said probe in water and in air in which the frequency of each electrode ring pair is assigned to zero when said electrode ring pair is proximal to water and assigned to 10,000 when said electrode ring pair is proximal to air.

27. The method as recited in claim 21 comprises the step of providing said probe as a fixed probe when inserted into said interceptor, and communicating said FOG, water, sludge, and air levels and identity via a low frequency radio signal to a receiver.

28. The method as recited in claim 21 comprises the step of providing a portable probe for temporary insertion into said interceptor and communicating said FOG, water, sludge, and air levels and identity via Bluetooth® LE to an external device including a phone, tablet, or computer hosting a software application written for both iOS and Android devices.

29. The method as recited in claim 21 comprises the steps of providing a fixed probe within said interceptor for continuous monitoring of said materials and levels, and communicating via LoRa to a gateway that connects via a cellular protocol to a web portal for said continuous monitoring of said materials and levels from a remote location.

30. The method as recited in claim 21 comprises the step of determining a length of said probe by the number of said sub-units daisy chained, one adjacent to another, each of said sub-units comprising a plurality of said electrode ring pairs coupled to a plurality of said timers and including a microcontroller for enabling said capacitance measurement converted to a frequency by each of said timers in a sequential manner.

* * * * *